United States Patent [19]
Fialkoff et al.

[11] 3,962,075
[45] June 8, 1976

[54] HEMO DIALYZER EMPLOYING TWO DIALYSATE SOLUTIONS

[75] Inventors: Sheldon L. Fialkoff, Brooklyn, N.Y.; Roy Alan Ackerman, Cambridge, Mass.

[73] Assignee: Tri-Flo Research Laboratories, Ltd., Jamaica, N.Y.

[22] Filed: Apr. 16, 1974

[21] Appl. No.: 461,461

Related U.S. Application Data

[63] Continuation-in-part of Ser. No. 395,675, Sept. 10, 1973, abandoned.

[52] U.S. Cl. ........................... 210/22 A; 210/321 A; 210/22 C; 210/321 B
[51] Int. Cl.² .................... B01D 31/00; B01D 13/00
[58] Field of Search ............................. 210/22, 321

[56] References Cited
UNITED STATES PATENTS

| | | | |
|---|---|---|---|
| 3,212,498 | 10/1965 | McKirdy et al. | 210/321 X |
| 3,352,779 | 11/1967 | Austin et al. | 210/23 |
| 3,412,865 | 11/1968 | Lontz et al. | 210/321 |
| 3,525,686 | 8/1970 | Roberts | 210/22 |
| 3,727,612 | 4/1973 | Sayers et al. | 210/22 X |
| 3,757,947 | 9/1973 | Wakefield et al. | 210/321 X |

FOREIGN PATENTS OR APPLICATIONS

| | | | |
|---|---|---|---|
| 1,198,032 | 7/1970 | United Kingdom | 210/321 |

*Primary Examiner*—Frank A. Spear, Jr.
*Attorney, Agent, or Firm*—Pollock, Vande Sande & Priddy

[57] ABSTRACT

A novel dialysis system is disclosed for both making and using a hemo dialyzer employing two novel dialysate solutions. The dialyzer per se used in the system comprises a clamp assembly enclosing three parallel plate dialyzer boards. Between each pair of boards a pair of semipermeable filtration media is enclosed. A total of six chambers is formed, three between each pair of dialyzer boards. The two chambers bounded by the semi-permeable filtration media form a portion of the flow path for the liquid to be dialyzed, in this case, blood. Of the remaining four chambers, two form a portion of a flow path of one dialysate solution and the other two chambers form a portion of the flow path for the remaining dialysate solution. Suitable connections are made on each of the boards for the introduction and withdrawal of the two dialysate solutions and suitable ports are provided to communicate with the membrane formed chambers for the introduction and withdrawal of the liquid to be dialyzed.

The two novel dialysate solutions are similar in that neither contain any concentration of urea. However, one of the dialysate solutions is hypertonic, that is, it contains a greater concentration of other constituents to be dialyzed than does the liquid to be dialyzed. The other dialysate solution is hypotonic with respect to the other constituents to be dialyzed, that is, it contains a lower concentration of these constituents than does the liquid to be dialyzed.

The rate of dialysis is greatly increased by the use of two different dialysate solutions as compared with the prior art processes which employ one dialysate solution. This greatly-increased dialysis rate enables the use of the parallel plate dialyzer, the use of which had substantially been discontinued.

19 Claims, 2 Drawing Figures

HEMO DIALYZER EMPLOYING TWO DIALYSATE SOLUTIONS

CROSS REFERENCE TO RELATED APPLICATION

This application is a continuation-in-part of prior copending application Ser. No. 395,675, filed Sept. 10, 1973, now abandoned.

BACKGROUND OF THE INVENTION

In the past 10 to 15 years the use of extracorporeal hemodialyzers in the treatment of patients with chronic renal insufficiency has become very popular. Otherwise known as "artificial kidneys" these devices supply the necessary missing renal function. The lack of this renal function would otherwise result in death of these patients. Other uses of artificial kidneys have been found for short-term use where renal function has been temporarily retarded due to the trauma of surgery of where renal function is insufficient due to the large scale ingestion of toxic substances.

To maintain the consistency of the human internal environment, the human kidney performs several functions. It detoxifies certain organic compounds, it synthesizes both hormones and enzymes, it excretes waste, and it also maintains the balances for water, electrolytes, acids and bases. In performing these functions, the kidney regulates the concentration of most of the constituents of the plasma; these include urea, uric acid, creatine, phenols, water, and the ions of sodium, potassium, calcium, magnesium, bicarbonate, chloride, phosphate, and sulfate. The artificial kidney performs one of these major functions, the removal from the body of certain potentially toxic substances all of which are soluble in water and adjust the levels of the blood constituents.

The prior art discloses a number of artificial kidneys which can be broadly classified into the parallel-plate dialyzers and coil-type dialyzers. For a description of the parallel-plate dialyzers see Kiil, "Development of a Parallel-flow Artificial Kidney in Plastics" Acta Chir. Scand. Supplement 23: 142, 1960. The coil type dialyzers have inherent disadvantages which make them less appealing than the parallel plate dialyzers. For instance, due to the large pressure drop in the blood flow path of the coil type dialyzers, it is normally necessary to employ a blood pump. The use of blood pumps results in serious complications. For one thing, they cause damage to blood cells and, in the treatment of chronic illnesses, this blood cell damage can ultimately affect the health of the patient. Furthermore, a large volume of blood is required to prime these units. This usually necessitates a transfusion with each treatment with the attendant cost and danger of infection. Notwithstanding the serious deficiencies of the coil-type dialyzers, they have substantially displaced the parallel plate dialyzers. The reason for this is the relatively long period of time required by parallel plate dialyzers to effect the required dialysis. For instance, the coil type dialyzer requires approximately 18 hours of treatment per week for an adult patient, usually three six-hour treatments. On the other hand, the parallel plate dialyzer requires twice this treatment time, 36 hours per week. As a result, there are essentially no parallel plate dialyzers in use today in the United States.

Because of the inherent advantages of the parallel plate dialyzers as opposed to the coil type dialyzer, the applicants thought it desirable to improve the parallel plate dialyzer to eliminate its drawbacks. Elimination of these drawbacks would enable practical use of the parallel plate dialyzer in order to enjoy the inherent advantages of this type of apparatus.

In order to enable utilization of the parallel plate dialyzer, we sought to increase the rate of dialysis by modifying the conventional parallel plate dialyzer and at the same time retaining the inherent advantages of this apparatus. The major modification made to the conventional dialyzer was to provide for the use of two dialysate solutions, one hypertonic and one hypotonic with respect to the blood. This modification in the dialysis process required modification of the dialyzer apparatus. Furthermore, in place of the conventional dialysate solution, we employ a novel hypotonic solution and a novel hypertonic dialysate solution. Experimental evidence indicates that the dialyzing apparatus disclosed in this application increases the rate of dialysis over the conventional parallel plate dialyzer by approximately six times and indeed, the dialyzing apparatus of the present invention operates at a faster rate than does the conventional coil dialyzer. Thus, applicants have succeed in overcoming the major disadvantage of the parallel plate dialyzer; its low rate of dialysis to the point where the parallel plate dialyzer of the present invention is not only comparable to the coil dialyzer in dialysis rate, but is actually faster than the coil dialyzer as well.

BRIEF DESCRIPTION OF THE DRAWINGS

As an aid in describing the present invention, reference is made to the accompanying drawing, in which like reference characters indicate similar apparatus, and in which.

DESCRIPTION OF THE INVENTION

Figure 1:
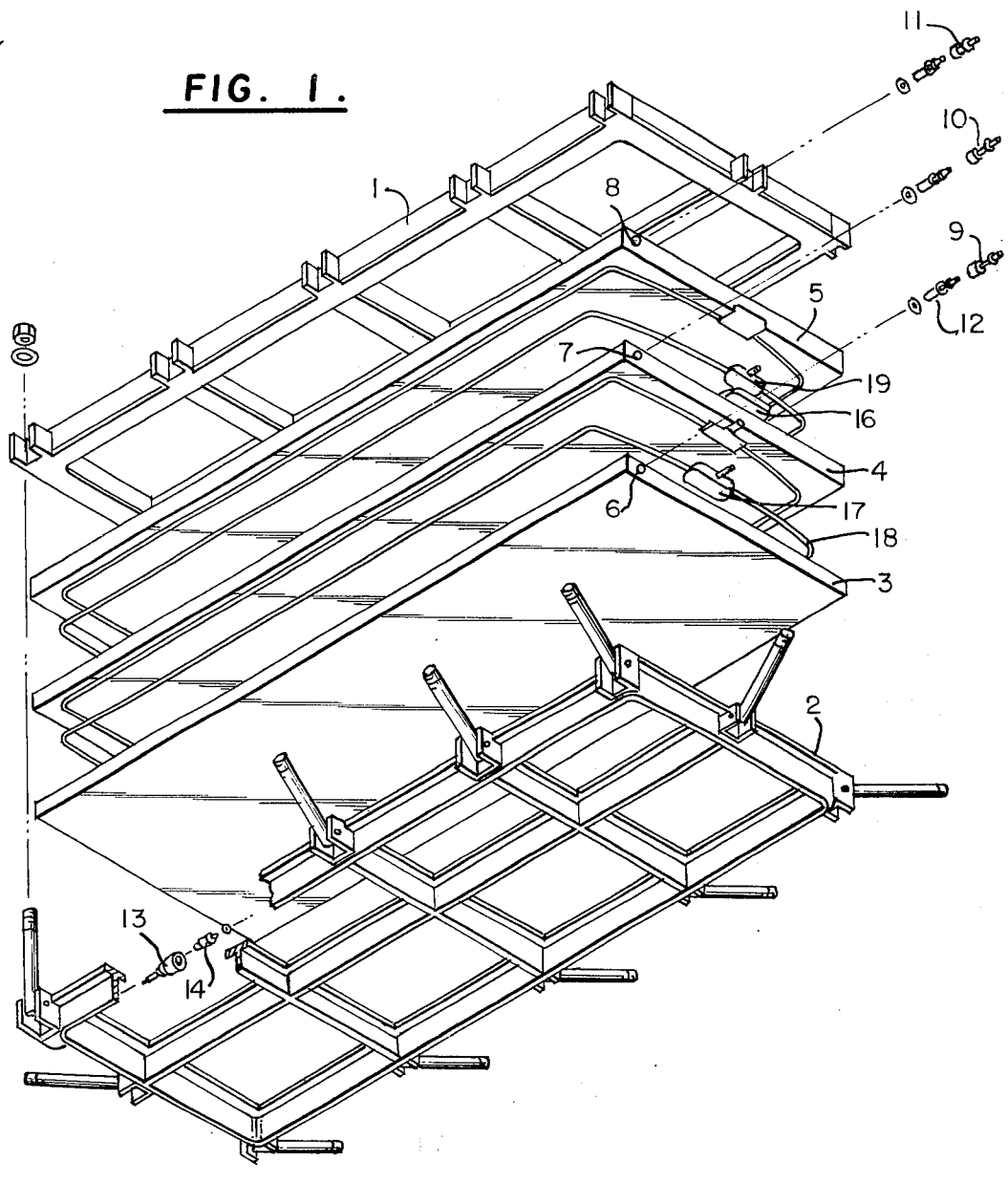
FIG. 1 is an exploded view of the dialyzer.

The apparatus used in the dialysis system of the present invention is shown, in exploded isometric view, in FIG. 1. Since, in large part, the dialyzer apparatus is conventional, description will be focused upon the areas in which the apparatus of the present invention departs from the conventional parallel plate dialyzer.

The parallel plate dialyzer comprises a pair of clamps, 1 and 2, which form the supporting structure for the dialyzer per se. The clamps 1 and 2, shown in FIG. 1, are not symmetrical. This, however, is not necessary so long as the longitudinally extending ribs 1a and 2a are not in the same plane as the blood ports 16 and 17. Suitable connecting means are shown in FIG. 1 so that the clamps exert a constant predetermined force upon the apparatus enclosed therein. Although FIG. 1 illustrates a nut and bolt connecting apparatus, other suitable connecting apparatus could also be used. Adjacent each of the clamps is one of dialyzer boards 3 and 5. Conventionally these boards are made of polypropylene and have a number of longitudinally extending surface grooves communicating between a pair of transversely disposed fluid connecting grooves, one at each end of the board. For reasons which will be explained hereinafter, the abovementioned grooves appear on only one surface of dialyzer boards 5 and 3, and appear on both faces of the board 4. The board 4 is stacked vertically between the boards 3 and 5. Interposed between each pair of boards are gaskets 18 and 19. Conventionally, during the assembly of this apparatus, a pair of semi-permeable membranes is interposed between each of the boards 3 and 4 and 4 and 5. This semi-permeable membrane performs filtration operations, such as osmosis and dialysis. Filtration media other than the semi-permeable membrane known to the prior art could be used. A Blood port, such as ports 17 and 16, is interposed between each pair of semi-permeable membranes.

In the conventional dialyzer, there is a single dialysate entrance port and a single dialysate exit port. The dialysate solution enters the dialysate entrance port in a board 5, for instance, and flows between the grooved surface of the board and its adjacent semi-permeable membrane. A pair of holes in the pair of semi-permeable membranes between the boards 4 and 5 communicates with the liquid collecting groove in board 5 so as to allow dialysate solution to flow down to and along the grooves on the upper face of board 4 between the board and its adjacent semi-permeable membrane. An additional communicating passage through the board 4 allows dialysate solution to flow down to the lower face of board 4 and between it and its adjacent semi-permeable membrane. A further pair of holes in the semi-permeable membranes between the boards 4 and 3 allows further dialysate solution to flow to the upper face of board 3 and along the upper groove face of board 3 between it and its adjacent semi-permeable membrane. A similar arrangement at the other end of the boards 3, 4, and 5 allows the dialysate solution to collect at the dialysate solution exit port in board 3.

In the dialysis system of the present invention the dialysate solution flow is restricted and additional dialysate ports are provided. In particular, in addition to dialysate inlet port 11, dialysate inlet ports 9 and 10 are also provided. The dialysate inlet port 11 provides ingress for flow of dialysate solution through inlet port 11 and adjacent one face of board 5. This dialysate solution is not allowed to flow adjacent board 4. Instead, inlet port 10 provides communication for dialysate solution to flow adjacent the upper and lower faces of board 4. In a like manner, dialysate inlet port 9 provides communication for dialysate solution to flow adjacent to the upper face of board 3. The conventional blood ports 16 and 17 provide inlet ports for the blood, or solution to be treated, to the dialyzer.

Dialysate solution exit port 13 is shown in FIG. 1 providing an exit for the dialysate solution flowing adjacent the upper face of board 3. Additional dialysate solution exit ports are provided, one for each of boards 4 and 5. In addition, of course, conventional blood ports are provided. However, neither the blood ports nor the two additional dialysate solution exit ports are shown in FIG. 1. Since the direction of blood flow is conventionally opposite to the direction of dialysate flow, the blood ports 16 and 17 are blood exit ports and the other blood ports (not illustrated) are entrance ports.

Figure 2:
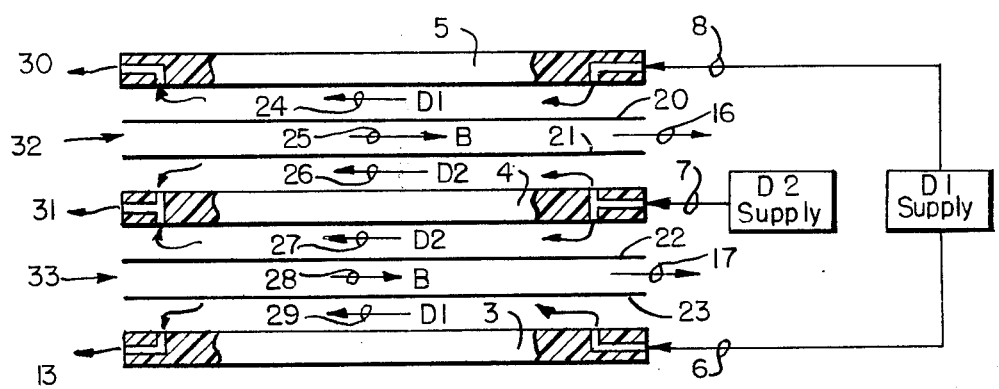
FIG. 2 is a cross-sectional schematic diagram indicating the flow paths of the dialyzer.

In order to understand the dialysis system of the present invention, FIG. 2 is a cross-sectional schematic showing of the dialyzer apparatus in operation. Reference characters 3, 4 and 5 refer to the dialyzer boards (also shown in FIG. 1). Board 5 has an inlet 8 provided to receive dialysate inlet port 11 (illustrated in FIG. 1). The inlet 8 provides a communication to the transversely extending dialysate solution collecting groove in the face of the dialyzer board 5. This latter groove communicates with longitudinally extending surface grooves conventional in such dialyzer boards. At the other end of dialyzer board 5 a second transversely disposed dialysate solution collecting groove is provided communicating with an exit 30. This exit is coupled to a dialysate solution exit line (not illustrated). Dialyzer board 4 is in many respects similar to the dialyzer board 5 except that it has longitudinally extending surface grooves on both upper and lower faces of the dialyzer board 4 and correspondingly has a pair of transversely disposed collecting grooves on each face of the board 4. The two transversely disposed fluid collecting grooves at one end of the board 4 communicate with dialysate inlet 7. The remaining two transversely disposed dialysate solution collecting grooves at the other end of the board 4 communicate with dialysate exit 31. The board 3 is a mirror image of the board 5, having an inlet 6 and an exit 13.

Disposed between the boards 4 and 5 are a pair of semi-permeable membranes 20 and 21. Likewise, disposed between boards 4 and 3 is another pair of semi-permeable membranes 22 and 23. Between the membranes 20 and 21 are disposed blood ports 16 and 32. Disposed between semi-permeable membranes 22 and 23 are blood ports 17 and 33.

The blood flow path in the dialyzer enters through blood ports 32 and 33. One blood flow path 25 exists between semi-permeable membranes 20 and 21 and this path includes blood exit port 16. A second blood flow path 28 exists between semi-permeable membranes 22 and 23 and communicates with blood exit port 17. The dialysate solution entering at inlet 8 flows in path 24 between semi-permeable membrane 20 and the board 5, and exits at exit 30. This dialysate solution will be referred to as D1. Another flow path 26 exists for dialysate solution between board 4 and semi-permeable membrane 21. This dialysate solution enters at inlet 7 and exits at 31 and will be referred to as D2. A further D2 dialysate solution flow pateh 27 is provided between inlet 7 and exit 31. This path is defined between the board 4 and semi-permeable membrane 22. Finally, dialysate solution flow path 29 exists for a dialysate solution D1 between semi-permeable membrane 23 and board 3. Inlet 6 and the exit 13 are associated with flow path 29.

The dialysate solutions D1 and D2 are respectively differing dialysate solutions. The solutions are contained in tanks and are fed or pumped (by gravity or pumps) into the respective dialysate flow paths. As shown in FIG. 2 the inlet 7 carries dialysate solution D2 while the inlets 6 and 8 carry dialysate solution D1. These latter two inlets can actually be coupled together from a single dialysate solution source. In like manner the exits 30 and 13 can be coupled together and coupled to a dialysate solution sink.

The novel hypotonic dialysate solution supports a dialysis mechanism similar in some respects to that carried out in conventional dialyzers. More particularly, the concentration gradient developed between the blood and the hypotonic dialysate solution with respect to urea and other constituent ions causes movement of these substances across the semi-permeable membranes. This results in a decrease in concentration of these substances in the blood. At the same time there is a urea concentration gradient between the blood and the hypertonic dialysate solution causing further urea movement out of the blood. Since the hypertonic dialysate solution has a higher concentration of other blood constituents than does the blood, a concentration gradient develops which carries these other constituent ions into the blood. This results in an increase in the concentrations of these ions in the blood.

Furthermore, and at the same time the system of hypotonic dialysate-membrane-blood-membrane-hypertonic dialysate produces still another gradient. This is an osmotic gradient due to the water concentration variations, resulting in a high velocity flow of water from the hypotonic dialysate through the blood to the hypertonic dialysate. We believe this latter, relatively high velocity, flow carries with it additional urea and other constituents and results in the improved dialysis rates proven in our tests.

In addition to the dialyzer apparatus per se, which has been discussed above, an actual dialyzer operation requires monitoring and control equipment for maintaining the temperature and concentration of both dialysate solutions and monitoring to detect any blood leakage into the dialysate flow paths which would indicate the presence of leaks in the system.

The apparatus discussed above can be utilized in either of two modes; a one-pass system or in a recirculating system. The terms refer to the dialysate flow paths. In the one-pass system, dialysate is pumped or fed (by gravity or otherwise) from a tank through the dialyzer and then discharged. In the recirculating system after the dialysate solution passes through the dialyzer it is continuously fed back to the dialysate tank. Clearly, the recirculating system uses less dialysate solution, but on the other hand, the concentrations of toxic substances in the dialysate solutions will gradually change as the toxic substances are removed from the blood and received by the dialysate solution. Therefore in a recirculating mode the rate of extraction of toxic substances, which depends upon the dialysate solution concentrations, will decrease. Against this must be balanced the added costs of dialysate solution in the one-pass system.

In order to effectively use the method and apparatus invented by applicants, it is necessary to provide two dialysate solutions, one which can be termed hypertonic and the other which can be termed hypotonic. Both solutions are similar in that neither contains any concentration of urea. As a result, the urea concentration in the impure blood provides a concentration gradient between the blood and both dialysate solutions which results in the extraction of urea from the impure blood. Furthermore, the apparatus can also be utilized to adjust the levels of various other blood constituents. This is a function which is also performed by a human kidney and which should be performed by an artificial kidney.

Conventional dialyzers also perform this function, although, as has been explained above, they employ only one dialysate solution. It is well understood in the art that the conventional dialysate solution must be adjusted in the light of each patient's blood composition. However, it is common practice in the field for manufacturers to provide artificial kidney treatment centers with a generic mixture which, when dissolved in a solvent, usually water, will provide a dialysate applicable to most patients. This dialysate solution can then be modified slightly in light of each particular patient's needs, if necessary. In using the instant invention, of course, two dialysate solutions are required, one hypertonic and one hypotonic. We have tested the invention with 15 liter batches of hypertonic and hypotonic solutions. The composition of these solutions is set forth below, by weight.

| Constituent | Hypertonic Solution Weight per 15 Liter Solution |
|---|---|
| Sodium chloride | 168.5 grams |
| Potassium chloride | 11.2 grams |
| Sodium bicarbonate | 60.4 grams |
| Sodium citrate | 0.8 grams |
| Sodium lactate | 2.0 millimeters |
| Dextrose | 60.0 grams |
| Calcium chloride | 12.1 grams |
| Magnesium chloride | 2.9 grams |
| Sodium acetate | 37.0 grams |
| Sodium chloride | 4.2 grams |
| Sodium bicarbonate | 15.8 grams |
| Sodium acetate | 9.2 grams |
| Potassium chloride | 1.7 grams |
| Dextrose | 60.0 grams* |
| Magnesium chloride | 0.75 grams |
| Calcium chloride | 1.6 grams |
| Sodium acetate | 9.25 grams |

*This may be reduced to 30.0 grams in accordance with the desired water ultrafiltration rate.

The weights given for calcium chloride are for the dihydrate type crystal. The weights for dextrose are given for anhydrous variety.

The value for these constituents are determined by balancing the hypertonic and hypotonic solutions about the desired constituent level. Normal blood has the following constituent ions at the following levels:

| Solute | Normal Blood Constituent Levels Level |
|---|---|
| NA+ | 135–145 mEq/liter |
| K+ | 3.5–5.5 mEq/liter |
| CA++ | 4.8–5.6 mEq/liter |
| Mg++ | 1.8–2.3 mEq/liter |
| Cl− | 97–105 mEq/liter |
| $HCO_3^-$ | 25–28 mEq/liter |
| PO4 | 3.0–4.5 mg/100 cc |
| SO4− | 1 mEq/liter |
| Urea | 5–20 mg/100 cc |
| Creatinine | 0.8–1.8 mg/100 cc |

Since the various concentration gradients are developed by ions and not compounds we set out below the ionic strengths achieved by our typical hypertonic and hypotonic solutions:

| Ions | Hypotonic (mEq/liter) | Hypertonic (mEq/liter) |
|---|---|---|
| Na+ | 27.69 | 283.62 |
| Ca++ | 0.96 | 7.27 |
| Mg++ | 0.52 | 2.02 |
| K+ | 1.52 | 10.00 |
| Cl− | 9.28 | 220.58 |
| $HCO_3^-$ | 12.50 | 47.90 |
| Citrate− | — | 0.25 |
| Lactate− | — | 1.67 |
| Acetate− | 10.40 | 41.80 |

Comparing the ionic strengths in the hypertonic and hypotonic solutions with the nominal ionic strengths for normal blood, illustrates the manner in which the hypertonic and hypotonic solutions are balanced about normal blood.

The solutions with the ionic strengths referred to above are well suited to in vivo dialysis. However, satisfactory dialysis can be achieved by employing hypertonic and hypotonic dialysate solutions whose only constituent ions are Na+, K+, Cl−, and $HCO_3^-$. Such a solution can be suitably prepared by employing only the following constituents: NaCl, KCl, $NaHCO_3$ and CaCl$_2$. These solutions, when properly prepared to be balanced about normal blood ionic strengths will have the following ionic strengths:

| Ions | Ionic Strength (mEq/liter) | |
|---|---|---|
| | Hypertonic | Hypotonic |
| Na$^+$ | 283.62 | 27.69 |
| Ca$^{++}$ | 7.27 | 0.96 |
| K$^+$ | 10.00 | 1.52 |
| Cl$^-$ | 220.58 | 9.28 |
| HCO$_3^-$ | 47.90 | 12.50 |

In addition to providing improved rate of dialysis this system has the further advantage of being self-limiting when used in a recirculating arrangement. Since the dialysate solutions are balanced around normal blood levels the concentration gradients for any ion will reduce as the ionic strength in the blood approaches the normal level. This will reduce the dialysis rate with respect to that constituent and provides a self-limited system.

We have carried out comparison testing in order to determine the comparative efficiency of the conventional parallel plate dialyzer and the dialyzer of our invention. In these tests the blood plasma was simulated and its flow rate was regulated at 139.42 cubic centimeters per minute. This flow rate is within the normal range of blood flow that would be expected in a parallel plate dialyzer as a result of normal blood pressure in the human body. The hypotonic solution was regulated at a flow rate of 585.85 cubic centimeters per minute and the hypertonic solution was regulated at a flow rate of 408.5 cubic centimeters per minute. In any actual application of the dialyzer of this invention, these flow rates are adjusted so that the rate of urea extraction is tolerable to the patient. That is, an upper limit exists for the dialysate solution flow rates which is the flow rate which results in a urea extraction rate which could be harmful to the patient. Furthermore the dialysis rate can be varied by varying these flow rates.

The results of the comparative effectiveness tests will now be set out. Results were obtained for two runs on a conventional parallel plate dialyzer and four runs using the dialyzer of the instant invention. Each run lasted 2 hours and 40 minutes. In the first run on the conventional parallel plate dialyzer, the plasma was simulated as follows, for a 15 liter batch: urea 225 grams, sodium chloride 84.2 grams, potassium chloride 5.6 grams, calcium chloride 12.1 grams, magnesium chloride 2.9 grams, sodium bicarbonate 30.2 grams, sodium lactate 1.0 milliliter, and sodium citrate 0.4 grams. The dialysate solution consisted of the following constituents in a 15 liter solution: sodium chloride 8.3 grams, sodium bicarbonate 31.5 grams, sodium acetate 18.5 grams, dextrose 60.0 grams, calcium chloride 3.2 grams, magnesium chloride 1.5 grams, and potassium chloride 3.4 grams. The second run on the conventional parallel plate dialyzer employed a simulated plasma consisting of the following constituents in a 15 liter solution: urea 225 grams, sodium chloride 84.2 grams, potassium chloride 5.6 grams, sodium bicarbonate 30.2 grams, sodium lactate 1.0 milliliter, and sodium citrate 0.4 grams. The dialysate solution consisted of the following constituents in a 15 liter solution: sodium chloride 8.3 grams, sodium bicarbonate 31.5 grams, sodium acetate 18.5 grams, and potassium chloride 3.4 grams.

At the conclusion of each of the runs, the urea concentration in the simulated plasma was measured to determine the effectiveness of the dialysis. In the first run the urea concentration was reduced 29.5% and in the second run the urea concentration was reduced 13.2%.

Four identical runs were made using the dialyzer system of the present invention. In each of these runs the plasma was simulated as follows in a 15 liter solution: urea 225 grams, sodium chloride 84.2 grams, potassium chloride 5.6 grams, sodium bicarbonate 30.2 grams, sodium lactate 1.0 milliliters and sodium citrate 0.4 grams. The hypertonic dialysate solution included the following constituents in a 15 liter solution: sodium chloride 168.5 grams, potassium chloride 11.2 grams, sodium bicarbonate 60.4 grams, sodium citrate 0.8 grams, and sodium lactate 2.0 milliliters. The hypotonic dialysate solution consisted of the following constituents in a 15 liter solution: sodium chloride 4.2 grams, sodium bicarbonate 15.8 grams, sodium acetate 9.2 grams, and potassium chloride 1.7 grams. Whenever calcium chloride has been referred to above, the weight was given for the dihydrate-type crystal. In the case of dextrose, the weights given are given for the anhydrous variety.

After each of the runs using the dialyzer of the present invention, the urea concentration in the simulated plasma was measured. In the first run the urea concentration was reduced 42.0%, in the second run it was reduced 42.9%, in the third run it was reduced 47.5%, and in the fourth run it was reduced 54.8%.

The average percent reduction in the urea concentration in the plasma using the dialyzer of the present invention was 46.8% and for the conventional parallel plate dialyzer it was 21.4%. A simple computation indicates that the dialyzer of the present invention is a 118.7% improvement upon the conventional parallel plate dialyzer. This is calculated as follows:

$$\frac{46.8\% - 21.4\%}{21.4\%} \times 100 = 118.7\%$$

It was previously mentioned that approximately 6 hours per week of treatment are required by the presently used coil type dialyzer. Extrapolating on the results achieved in our tests, if the conventional parallel plate dialyzer was used for 6 hours, it would decrease the urea concentration in the blood to about 55% of its initial value. (Since the relationship between time and percent reduction of urea is logarithmic the extrapolations expressed here are not linear.) The widely used coil type device, in about the same period of time, decreases the urea concentration level to about 21% of its initial value. However, if the dialyzer disclosed herein were employed for six hours of treatment, the urea level would decrease to approximately 7.5% of its initial value during a 6 hour treatment period. This indicates a 585% improvement over the conventional parallel plate device and a 163% improvement over the coil type dialyzer.

Thus, the dialysis system of this invention is shown to have eliminated the single significant drawback in conventional parallel plate dialyzers, i.e., rate of dialysis. The dialysis system disclosed herein increases the dialysis rate over the conventional parallel plate dialyzers to a point where the dialysis rate is comparable to, or even greater than, the dialysis rate of the predominantly used coil type device. The inherent advantages of the parallel plate dialyzer, i.e., avoiding use of a blood pump, minimal priming blood requirement, decreasing the necessity for transfusions and simplicity should make the dialyzer disclosed herein a more attractive alternative than the coil type device. Furthermore, a great many conventional parallel plate dialyzers exist today in the United States which are currently not in use. Although the dialysis system disclosed herein doubles the dialysis rate in comparison to the conventional parallel plate dialyzer, a conventional parallel plate dialyzer can be modified so as to utilize the principles disclosed in this application. It is only necessary to add dialysate inlet and exit ports to the boards which do not already have these. The conventional parallel plate dialyzers also had a communicating path from the upper surface of the middle board to the lower surface of the middle board and it will be necessary to block this communicating path. Conventionally, holes were punched in the filtration media to link up with this communicating path in the middle dialyzer board. When using a dialyzer in accordance with the teachings of this application, this hole should no longer be made, that is, the filtration media should be used without making any perforations therein. Providing such a modified dialyzer with two dialysate solutions as disclosed in this application, will result in a dialyzer operating in accordance with the principles we are here teaching. This relatively minor modification to the conventional parallel plate dialyzers which exist today, makes this modification an attractive alternative or supplement to manufacturing additional dialyzers.

Although FIGS. 1 and 2, using three dialyzer boards, are essentially two different dialyzers in parallel, it will be understood by those skilled in the art that only two boards could be used without departing from the spirit or scope of the present invention. Alternatively, if it were necessary, further bords could be utilized to in effect multiply the number of dialyzer elements, operating in parallel, without departing from the spirit or scope of the present invention.

We have also found that acetate and bicarbonate are, equivalent insofar as each enters the dialysis processes. As a result either one or the other may be omitted by suitably adjusting the level of the remaining constituent.

In addition, although we have disclosed mole-equivalents, grams and other values to figures of two decimal places, under practical conditions single decimal figure tolerances are sufficient.

What we claim is:

1. A method of purifying blood in which blood is subjected to filtration to remove impurities therefrom, said filtration comprising,
    exposing blood between two zones, the first zone containing a hypotonic solution with respect to blood constituents, both said zones being separated from said flow of blood by a semi-permeable filtration medium, the hypotonic solution being at a concentration sufficient to remove at least a portion of said blood impurities,
    the improvement comprising providing a hypertonic solution in said second zones, said hypertonic solution being hypertonic with respect to said blood constituents other than urea, both said hypertonic and hypotonic solutions having constituents in common with blood but at concentrations different therefrom to produce a concentration gradient with respect to said constituents, said concentrations being highest in said hypertonic solution and lowest in said hypotonic solution.
    whereby said concentration gradient produces an efflux of water from said blood by reason of the osmotic gradient which flow carries with it blood impurities effective to increase the dialysis rate.

2. A composition of matter which, when dissolved in solution, will form a hypertonic solution useful in dialysis of blood, comprising the following constituents per 15 liters of solvent:

| | |
|---|---|
| Sodium chloride | 168.5 g |
| Potassium chloride | 11.2 g |
| Sodium bicarbonate | 60.4 g |
| Sodium citrate | 0.8 g |
| Sodium lactate | 2.0 ml |
| Dextrose | 60.0 g |
| Calcium chloride | 12.1 g |
| Magnesium chloride | 2.9 g |
| Sodium acetate | 37.0 g |

3. A composition of matter which, when dissolved in solution, will form a hypotonic solution useful in dialysis of blood comprising the following constituents per 15 liters of solvent:

| | |
|---|---|
| Sodium chloride | 4.2 g |
| Potassium chloride | 1.7 g |
| Sodium bicarbonate | 15.8 g |
| Dextrose | 60.0 g |
| Calcium chloride | 1.6 g |
| Magnesium chloride | 0.8 g |
| Sodium acetate | 9.2 g |

4. A composition of matter which, when dissolved in solution, will form a hypertonic solution useful in dialysis of blood, said composition of matter providing a solution with the following mole equivalents per liter ionic strengths:

| | |
|---|---|
| $Na^+$ | 283.6 |
| $Ca^{++}$ | 7.3 |
| $K^+$ | 10.0 |
| $Cl^-$ | 220.5 |
| $HCO_3^-$ | 47.9 |

5. The composition of claim 4 which further provides a solution including the following ions at the listed ionic strengths:

| | |
|---|---|
| $Mg^{++}$ | 2.0 |
| $Citrate^-$ | 0.3 |
| $Lactate^-$ | 1.7 |
| $Acetate^-$ | 41.8 |

6. A composition of matter which, when dissolved in solution, will form a hypotonic solution useful in dialysis of blood, said composition of matter providing a solution with the following mole equivalents per liter of ionic constituents:

| | |
|---|---|
| $Na^+$ | 27.7 |
| $Ca^{++}$ | 1.0 |
| $K^+$ | 1.5 |
| $Cl^-$ | 9.3 |
| $HCO_3^-$ | 12.5 |

7. The composition of claim 6 which further provides a solution including the following ions at the listed ionic strengths:

| | |
|---|---|
| $Mg^{++}$ | 0.5 |
| $Acetate^-$ | 10.4. |

8. A hypertonic solution useful in the dialysis of blood comprising the following constituents at the listed ionic strength:

| | |
|---|---|
| $Na^+$ | 283.6 mole equivalents/liter |
| $Ca^{++}$ | 7.3 mole equivalents/liter |
| $K^+$ | 10.0 mole equivalents/liter |
| $Cl^-$ | 220.6 mole equivalents/liter |
| $HCO_3^-$ | 47.9 mole equivalents/liter. |

9. The hypertonic solution of claim 8 which also comprises:

| | |
|---|---|
| $Mg^{++}$ | 2.0 mole equivalents/liter |
| $Citrate^-$ | 0.3 mole equivalents/liter |
| $Lactate^-$ | 1.7 mole equivalents/liter |
| $Acetate^-$ | 41.8 mole equivalents/liter. |

10. A hypotonic solution useful in the dialysis of blood comprising the following constituents at the listed ionic strengths:

| | |
|---|---|
| $Na^+$ | 27.7 mole equivalents/liter |
| $Ca^{++}$ | 1.0 mole equivalents/liter |
| $K^+$ | 1.5 mole equivalents/liter |
| $Cl^-$ | 9.3 mole equivalents/liter |
| $HCO_3^-$ | 12.5 mole equivalents/liter. |

11. The hypotonic solution of claim 10 which also comprises

| | |
|---|---|
| $Mg^{++}$ | 0.5 mole equivalents/liter |
| $Acetate^-$ | 10.4 mole equivalents/liter. |

12. A dialysis system for the dialysis of a liquid comprising at least a pair of board means and,
a flow path adapted to communicate with a supply of a liquid to be dialyzed,
said flow path including a segment in which said liquid flowing in said path is subject to dialysis,
a pair of semi-permeable filtration media defining said segment of said liquid flow path,
a first dialysate flow path including a hypertonic dialysate solution and having a dialysis segment defined by one of said pair of semi-permeable filtration media and one of said board means,
a second dialysate flow path independent of and separate from said first dialysate flow path including a hypotonic dialysate solution and having a dialysis segment defined by said other of said pair of semi-permeable filtration media and said other board means, both said hypertonic and said hypotonic dialysate solutions including constituents in common with said liquid but at concentrations different therefrom to produce a concentration gradient with respect to said constituents, said concentration being highest in said hypertonic dialysate and lowest in said hypotonic dialysate,
said concentration gradient effective to increase the dialysis rate of said system.

13. The system of claim 12 further including first and second dialysate supply means,
said first dialysate flow path connected to said first dialysate supply means,
and said second dialysate flow path connected to said second dialysate supply means.

14. The system of claim 12 wherein said one board means comprises a board with at least one inlet and outlet therein, said inlet and outlet connected in a first dialysate flow path,
said other board means comprising a second board with at least one inlet and outlet, said inlet and outlet connected in a second dialysate flow path.

15. The system of claim 12 wherein said hypertonic and hypotonic dialysate each comprises a solution with the following ionic constituents:
$Na^+$
$Ca^{++}$
$K^+$
$Cl^-$
$HCO_3^-$
and wherein said ionic strengths are greater in said hypertonic solution than in said hypotonic solution.

16. The system of claim 15 wherein said hypertonic dialysate solution also comprises the following ionic constituents:
$Mg^{++}$
$Citrate^-$
$Lactate^-$
$Acetate^-$.

17. An artificial kidney for the dialysis of blood comprising at least a pair of board means and,
a blood flow path adapted to communicate with the blood supply of a patient,
said blood flow path including a segment in which the blood flowing in said path is subject to dialysis,
a pair of semi-permeable filtration media defining said segment of said blood flow path,
a hypertonic dialysate flow path including a hypertonic dialysate, said hypertonic dialysate being hypertonic with respect to blood constituents other than urea, said hypertonic dialysate flow path having a dialysis segment defined by one of said pair of semi-permeable filtration media and one of said board means,
a hypotonic dialysate flow path independent of, and seperate from, said hypertonic dialysate flow path including a hypotonic dialysate which is hypotonic with respect to blood constituents, said hypotonic dialysate flow path having a dialysis segment defined by said other of said pair of semi-permeable filtration media and said other board means,
said hypertonic and hypotonic dialysates comprising constiuents in common with blood but at concentrations different therefrom to provide a concentration gradient from hypertonic dialysate to blood to hypotonic dialysate with respect to each of said common constituents, said concentration gradient effective to increase the dialysis rate of said artificial kidney.

18. The apparatus of claim 17 further including hypertonic and hypotonic dialysate supply means,
said hypertonic dialysate flow path connected to said hypertonic dialysate supply means, and
said hypotonic dialysate flow path connected to said hypotonic dialysate supply means.

19. The apparatus of claim 17 wherein said one board means comprises a board with at least one inlet and outlet therein, said inlet and outlet connected in said hypertonic dialysate flow path,
said other board means comprising a second board with at least one other inlet and outlet, said other inlet and outlet connected in said hypotonic dialysate flow path.

* * * * *